(12) United States Patent
Stone et al.

(10) Patent No.: US 7,857,830 B2
(45) Date of Patent: Dec. 28, 2010

(54) SOFT TISSUE REPAIR AND CONDUIT DEVICE

(75) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 517 days.

(21) Appl. No.: 11/869,440

(22) Filed: Oct. 9, 2007

(65) Prior Publication Data

US 2008/0027446 A1    Jan. 31, 2008

Related U.S. Application Data

(63) Continuation-in-part of application No. 11/347,661, filed on Feb. 3, 2006, now Pat. No. 7,749,250, and a continuation-in-part of application No. 11/408,282, filed on Apr. 20, 2006, now abandoned.

(60) Provisional application No. 60/885,062, filed on Jan. 16, 2007, provisional application No. 60/885,057, filed on Jan. 16, 2007.

(51) Int. Cl.
*A61B 17/04* (2006.01)
*A61B 17/84* (2006.01)
*A61F 2/08* (2006.01)

(52) U.S. Cl. ........................ 606/232; 600/300
(58) Field of Classification Search ............... 606/300, 606/213, 215, 216, 232, 60, 74, 151; 632/13.11, 632/14.12
See application file for complete search history.

(56) References Cited

U.S. PATENT DOCUMENTS

| | | | |
|---|---|---|---|
| 26,501 A | 12/1859 | Kendrick et al. | |
| 65,499 A | 6/1867 | Miller | |
| 126,366 A | 4/1872 | Wills | |
| 233,475 A | 10/1880 | Cook et al. | |

(Continued)

FOREIGN PATENT DOCUMENTS

AU    4957264    3/1966

(Continued)

OTHER PUBLICATIONS

A. Weiler, et al; Biodegradierbare Interferenzschrauben in der Kreuzbandchirurgie; Op-Journal 14 pp. 278-284; 1998.

(Continued)

*Primary Examiner*—(Jackie) Tan-Uyen T Ho
*Assistant Examiner*—Dianne Dornbusch
(74) *Attorney, Agent, or Firm*—Harness, Dickey

(57) ABSTRACT

A soft tissue repair method. The method includes providing a flaccid tubular member having a longitudinal bore and first and second ends, the tubular member defining first and second portions integral with the tubular member. The method includes coupling the tubular member to a flexible strand, inserting the tubular member from a first side of the soft tissue to a second side of soft tissue, such that a first portion of the tubular member exits the second side of the soft tissue and a second portion of the tubular member remains inside the soft tissue, tensioning the flexible strand, deforming the first portion of the tubular member to an anchoring shape, and forming a vascularization conduit from the second portion of the tubular member.

18 Claims, 5 Drawing Sheets

U.S. PATENT DOCUMENTS

| | | |
|---|---|---|
| 261,501 A | 7/1882 | Vandermark |
| 417,805 A | 12/1889 | Beaman |
| 487,304 A | 12/1892 | Todd |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A * | 9/1971 | Barry .................. 128/898 |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A * | 9/1977 | Barry ............... 623/15.11 |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |

| | | | | | |
|---|---|---|---|---|---|
| 4,175,555 A | 11/1979 | Herbert et al. | 4,690,169 A | 9/1987 | Jobe |
| 4,185,636 A | 1/1980 | Gabbay et al. | 4,705,040 A | 11/1987 | Mueller et al. |
| 4,196,883 A | 4/1980 | Einhorn et al. | 4,708,132 A | 11/1987 | Silvestrini |
| 4,210,148 A | 7/1980 | Stivala | 4,716,893 A | 1/1988 | Fischer et al. |
| 4,235,161 A | 11/1980 | Kunreuther | 4,719,671 A | 1/1988 | Ito et al. |
| 4,235,238 A | 11/1980 | Ogiu et al. | 4,719,917 A | 1/1988 | Barrows et al. |
| 4,237,779 A | 12/1980 | Kunreuther | 4,723,540 A | 2/1988 | Gilmer, Jr. |
| 4,243,037 A | 1/1981 | Smith | 4,724,839 A | 2/1988 | Bedi et al. |
| 4,249,525 A | 2/1981 | Krzeminski | 4,728,332 A | 3/1988 | Albrektsson et al. |
| 4,263,913 A | 4/1981 | Malmin | 4,738,255 A | 4/1988 | Goble et al. |
| 4,265,246 A | 5/1981 | Barry | 4,741,330 A | 5/1988 | Hayhurst |
| 4,273,117 A | 6/1981 | Neuhauser et al. | 4,741,336 A | 5/1988 | Failla et al. |
| 4,275,717 A | 6/1981 | Bolesky | 4,744,353 A | 5/1988 | McFarland |
| 4,287,807 A | 9/1981 | Pacharis et al. | 4,744,793 A | 5/1988 | Parr et al. |
| 4,291,698 A | 9/1981 | Fuchs et al. | 4,750,492 A | 6/1988 | Jacobs |
| 4,301,551 A | 11/1981 | Dore et al. | 4,760,843 A | 8/1988 | Fischer et al. |
| 4,312,337 A | 1/1982 | Donohue | 4,760,848 A | 8/1988 | Hasson |
| 4,316,469 A | 2/1982 | Kapitanov et al. | 4,772,261 A | 9/1988 | Von Hoff et al. |
| 4,326,531 A | 4/1982 | Shimonaka et al. | 4,772,286 A | 9/1988 | Goble et al. |
| 4,345,601 A | 8/1982 | Fukuda | 4,773,910 A | 9/1988 | Chen et al. |
| 4,349,027 A | 9/1982 | DiFrancesco | 4,775,380 A | 10/1988 | Seedhom et al. |
| 4,388,921 A | 6/1983 | Sutter et al. | 4,776,328 A | 10/1988 | Frey et al. |
| 4,400,833 A | 8/1983 | Kurland | 4,781,190 A | 11/1988 | Lee et al. |
| 4,402,445 A | 9/1983 | Green | 4,784,126 A | 11/1988 | Hourahane et al. |
| 4,409,974 A | 10/1983 | Freedland | 4,787,882 A | 11/1988 | Claren et al. |
| 4,438,769 A | 3/1984 | Pratt et al. | 4,790,297 A | 12/1988 | Luque et al. |
| 4,441,489 A | 4/1984 | Evans et al. | 4,793,363 A | 12/1988 | Ausherman et al. |
| 4,454,875 A | 6/1984 | Pratt et al. | 4,809,695 A | 3/1989 | Gwathmey et al. |
| 4,462,395 A | 7/1984 | Johnson | 4,813,406 A | 3/1989 | Ogle, II |
| 4,463,753 A | 8/1984 | Gustilo | 4,823,794 A | 4/1989 | Pierce |
| 4,473,102 A | 9/1984 | Ohman et al. | 4,828,562 A | 5/1989 | Kenna |
| 4,484,570 A | 11/1984 | Sutter et al. | 4,832,026 A | 5/1989 | Jones |
| 4,493,323 A | 1/1985 | Albright et al. | 4,834,098 A | 5/1989 | Jones |
| 4,496,468 A | 1/1985 | House et al. | 4,838,282 A | 6/1989 | Strasser et al. |
| 4,505,274 A | 3/1985 | Speelman | 4,841,960 A | 6/1989 | Garner |
| 4,509,516 A | 4/1985 | Richmond | 4,851,005 A | 7/1989 | Hunt et al. |
| 4,531,522 A | 7/1985 | Bedi et al. | 4,858,608 A | 8/1989 | McQuilkin et al. |
| 4,532,926 A | 8/1985 | O'Holla | 4,860,513 A | 8/1989 | Whitman |
| 4,534,350 A | 8/1985 | Golden et al. | 4,863,383 A | 9/1989 | Grafelmann et al. |
| 4,535,764 A | 8/1985 | Ebert | 4,870,957 A | 10/1989 | Goble et al. |
| 4,537,185 A | 8/1985 | Stednitz | 4,873,976 A | 10/1989 | Schreiber |
| 4,549,652 A | 10/1985 | Free | 4,887,601 A | 12/1989 | Richards |
| 4,561,432 A | 12/1985 | Mazor | 4,890,615 A | 1/1990 | Caspari et al. |
| 4,564,007 A | 1/1986 | Coombs et al. | 4,893,619 A | 1/1990 | Dale et al. |
| 4,570,623 A | 2/1986 | Ellison et al. | 4,893,974 A | 1/1990 | Fischer et al. |
| 4,573,844 A | 3/1986 | Smith | 4,895,148 A | 1/1990 | Bays et al. |
| 4,576,608 A | 3/1986 | Homsy | 4,896,668 A | 1/1990 | Popoff et al. |
| 4,584,722 A | 4/1986 | Levy et al. | 4,898,156 A | 2/1990 | Gatturna et al. |
| 4,590,928 A | 5/1986 | Hunt et al. | 4,899,743 A | 2/1990 | Nicholson et al. |
| 4,595,007 A | 6/1986 | Mericle | 4,901,721 A | 2/1990 | Hakki |
| 4,596,249 A | 6/1986 | Freda et al. | 4,923,461 A | 5/1990 | Caspari et al. |
| 4,602,635 A | 7/1986 | Mulhollan et al. | 4,927,421 A | 5/1990 | Goble et al. |
| 4,602,636 A | 7/1986 | Noiles | 4,946,468 A | 8/1990 | Li |
| 4,604,997 A | 8/1986 | De Bastiani et al. | 4,950,270 A | 8/1990 | Bowman et al. |
| 4,605,414 A | 8/1986 | Czajka | 4,950,285 A | 8/1990 | Wilk |
| 4,616,650 A | 10/1986 | Green et al. | 4,960,381 A | 10/1990 | Niznick |
| 4,621,640 A | 11/1986 | Mulhollan et al. | 4,961,741 A | 10/1990 | Hayhurst |
| 4,624,254 A | 11/1986 | McGarry et al. | 4,968,315 A | 11/1990 | Gatturna |
| 4,632,100 A | 12/1986 | Somers et al. | 4,968,317 A | 11/1990 | Tormala et al. |
| 4,635,637 A | 1/1987 | Schreiber | 4,969,886 A | 11/1990 | Cziffer et al. |
| 4,636,121 A | 1/1987 | Miller | 4,976,736 A | 12/1990 | White et al. |
| 4,641,652 A | 2/1987 | Hutterer et al. | 4,978,350 A | 12/1990 | Wagenknecht et al. |
| 4,649,952 A | 3/1987 | Jobe | 4,979,956 A | 12/1990 | Silvestrini |
| 4,653,486 A | 3/1987 | Coker | 4,983,176 A | 1/1991 | Cushman et al. |
| 4,653,487 A | 3/1987 | Maale | 4,988,351 A | 1/1991 | Paulos et al. |
| 4,653,489 A | 3/1987 | Tronzo | 4,994,074 A | 2/1991 | Bezwada et al. |
| 4,655,777 A | 4/1987 | Dunn et al. | 4,997,433 A | 3/1991 | Goble et al. |
| 4,662,068 A | 5/1987 | Polonsky | 5,002,550 A | 3/1991 | Li |
| 4,667,662 A | 5/1987 | Titone et al. | 5,002,562 A | 3/1991 | Oberlander |
| 4,667,675 A | 5/1987 | Davis | 5,007,921 A | 4/1991 | Brown |
| 4,669,473 A | 6/1987 | Richards et al. | 5,030,224 A | 7/1991 | Wright et al. |
| 4,683,895 A | 8/1987 | Pohndorf | 5,037,422 A | 8/1991 | Hayhurst et al. |
| 4,688,561 A | 8/1987 | Reese | 5,041,129 A | 8/1991 | Hayhurst et al. |

| | | | | | | |
|---|---|---|---|---|---|---|
| 5,046,513 A | 9/1991 | Gatturna et al. | | 5,290,217 A | 3/1994 | Campos |
| 5,047,030 A | 9/1991 | Draenert et al. | | 5,306,301 A | 4/1994 | Graf et al. |
| 5,053,046 A | 10/1991 | Janese | | 5,312,422 A | 5/1994 | Trott |
| 5,053,047 A | 10/1991 | Yoon | | 5,312,438 A | 5/1994 | Johnson |
| 5,059,201 A | 10/1991 | Asnis | | 5,318,577 A | 6/1994 | Li |
| 5,059,206 A | 10/1991 | Winters | | 5,318,578 A | 6/1994 | Hasson |
| 5,062,344 A | 11/1991 | Gerker | | 5,320,115 A | 6/1994 | Kenna |
| 5,062,843 A | 11/1991 | Mahony, III | | 5,320,626 A | 6/1994 | Schmieding |
| 5,078,731 A | 1/1992 | Hayhurst | | 5,320,633 A | 6/1994 | Allen et al. |
| 5,078,843 A | 1/1992 | Pratt | | 5,324,308 A | 6/1994 | Pierce |
| 5,084,050 A | 1/1992 | Draenert et al. | | 5,334,204 A | 8/1994 | Clewett et al. |
| 5,084,058 A | 1/1992 | Li | | 5,336,229 A | 8/1994 | Noda |
| 5,085,661 A | 2/1992 | Moss | | 5,336,231 A | 8/1994 | Adair |
| 5,087,263 A | 2/1992 | Li | | 5,336,240 A | 8/1994 | Metzler et al. |
| 5,092,866 A | 3/1992 | Breard et al. | | 5,342,369 A | 8/1994 | Harryman, II |
| 5,098,435 A | 3/1992 | Stednitz et al. | | 5,346,462 A | 9/1994 | Barber |
| 5,100,415 A | 3/1992 | Hayhurst | | 5,354,298 A | 10/1994 | Lee et al. |
| 5,100,417 A | 3/1992 | Cerier et al. | | 5,356,413 A | 10/1994 | Martins et al. |
| 5,116,337 A | 5/1992 | Johnson | | 5,358,511 A | 10/1994 | Gatturna et al. |
| 5,116,373 A | 5/1992 | Jakob et al. | | 5,360,431 A | 11/1994 | Puno et al. |
| 5,116,375 A | 5/1992 | Hofmann | | 5,362,294 A | 11/1994 | Seitzinger |
| 5,123,913 A | 6/1992 | Wilk et al. | | 5,364,400 A | 11/1994 | Rego, Jr. et al. |
| 5,127,785 A | 7/1992 | Faucher et al. | | 5,368,599 A | 11/1994 | Hirsch et al. |
| 5,129,901 A | 7/1992 | Decoste | | 5,370,661 A | 12/1994 | Branch |
| 5,129,902 A | 7/1992 | Goble et al. | | 5,370,662 A | 12/1994 | Stone et al. |
| 5,129,904 A | 7/1992 | Illi et al. | | 5,372,146 A | 12/1994 | Branch |
| 5,129,906 A | 7/1992 | Ross et al. | | 5,372,604 A | 12/1994 | Trott |
| 5,139,499 A | 8/1992 | Small et al. | | 5,372,821 A | 12/1994 | Badylak et al. |
| 5,139,520 A | 8/1992 | Rosenberg | | 5,374,268 A | 12/1994 | Sander |
| 5,143,498 A | 9/1992 | Whitman | | 5,379,492 A | 1/1995 | Glesser |
| 5,147,362 A | 9/1992 | Goble | | 5,383,878 A | 1/1995 | Roger et al. |
| 5,149,329 A | 9/1992 | Richardson | | 5,383,904 A * | 1/1995 | Totakura et al. ............. 606/228 |
| 5,152,790 A | 10/1992 | Rosenberg et al. | | 5,391,171 A | 2/1995 | Schmieding |
| 5,154,189 A | 10/1992 | Oberlander | | 5,391,176 A | 2/1995 | de la Torre |
| 5,156,616 A | 10/1992 | Meadows et al. | | 5,393,302 A | 2/1995 | Clark et al. |
| 5,163,960 A | 11/1992 | Bonutti | | RE34,871 E | 3/1995 | McGuire et al. |
| D331,626 S | 12/1992 | Hayhurst et al. | | 5,397,356 A | 3/1995 | Goble et al. |
| 5,169,400 A | 12/1992 | Muhling et al. | | 5,403,328 A | 4/1995 | Shallman |
| 5,176,682 A | 1/1993 | Chow | | 5,403,329 A | 4/1995 | Hinchcliffe |
| 5,178,629 A | 1/1993 | Kammerer | | 5,403,348 A | 4/1995 | Bonutti |
| 5,183,458 A | 2/1993 | Marx | | 5,417,691 A * | 5/1995 | Hayhurst .................... 606/232 |
| 5,192,282 A | 3/1993 | Draenert et al. | | 5,417,712 A | 5/1995 | Whittaker et al. |
| 5,197,987 A | 3/1993 | Koch et al. | | 5,423,819 A | 6/1995 | Small et al. |
| 5,203,784 A | 4/1993 | Ross et al. | | 5,423,823 A | 6/1995 | Schmieding |
| 5,203,787 A | 4/1993 | Noblitt et al. | | 5,423,860 A | 6/1995 | Lizardi et al. |
| 5,207,679 A | 5/1993 | Li | | 5,425,733 A | 6/1995 | Schmieding |
| 5,209,753 A | 5/1993 | Biedermann et al. | | 5,425,766 A | 6/1995 | Bowald |
| 5,209,805 A | 5/1993 | Spraggins | | 5,433,751 A | 7/1995 | Christel et al. |
| 5,211,647 A | 5/1993 | Schmieding | | 5,437,680 A | 8/1995 | Yoon |
| 5,211,650 A | 5/1993 | Noda | | 5,439,684 A | 8/1995 | Prewett et al. |
| 5,214,987 A | 6/1993 | Fenton, Sr. | | 5,443,468 A | 8/1995 | Johnson |
| 5,219,359 A | 6/1993 | McQuilkin et al. | | 5,443,482 A | 8/1995 | Stone et al. |
| 5,224,946 A | 7/1993 | Hayhurst et al. | | 5,443,483 A | 8/1995 | Kirsch et al. |
| 5,230,699 A | 7/1993 | Grasinger | | 5,443,509 A | 8/1995 | Boucher et al. |
| 5,232,436 A | 8/1993 | Janevski | | 5,445,833 A | 8/1995 | Badylak et al. |
| 5,234,435 A | 8/1993 | Seagrave, Jr. | | 5,447,512 A | 9/1995 | Wilson et al. |
| 5,235,238 A | 8/1993 | Nomura et al. | | 5,451,203 A | 9/1995 | Lamb |
| 5,236,445 A | 8/1993 | Hayhurst et al. | | 5,454,811 A | 10/1995 | Huebner |
| 5,236,461 A | 8/1993 | Forte | | 5,456,685 A | 10/1995 | Huebner |
| 5,242,447 A | 9/1993 | Borzone | | 5,456,722 A | 10/1995 | McLeod et al. |
| 5,246,441 A | 9/1993 | Ross et al. | | 5,458,601 A | 10/1995 | Young, Jr. et al. |
| 5,249,899 A | 10/1993 | Wilson | | 5,458,604 A | 10/1995 | Schmieding |
| 5,258,015 A | 11/1993 | Li et al. | | 5,462,560 A | 10/1995 | Stevens |
| 5,258,016 A | 11/1993 | DiPoto et al. | | 5,464,426 A | 11/1995 | Bonutti |
| 5,258,040 A | 11/1993 | Bruchman et al. | | 5,464,427 A | 11/1995 | Curtis et al. |
| 5,268,001 A | 12/1993 | Nicholson et al. | | 5,464,440 A | 11/1995 | Johansson et al. |
| 5,269,160 A | 12/1993 | Wood | | 5,466,237 A | 11/1995 | Byrd, III et al. |
| 5,269,783 A | 12/1993 | Sander | | 5,467,786 A | 11/1995 | Allen et al. |
| 5,269,809 A * | 12/1993 | Hayhurst et al. ............ 606/232 | | 5,470,334 A | 11/1995 | Ross et al. |
| 5,281,422 A | 1/1994 | Badylak et al. | | 5,470,337 A | 11/1995 | Moss |
| 5,282,809 A | 2/1994 | Kammerer et al. | | 5,470,338 A | 11/1995 | Whitfield et al. |
| 5,282,832 A | 2/1994 | Toso et al. | | 5,472,452 A | 12/1995 | Trott |
| 5,285,040 A | 2/1994 | Brandberg et al. | | 5,474,565 A | 12/1995 | Trott |

| | | | | | |
|---|---|---|---|---|---|
| 5,474,568 A | 12/1995 | Scott | 5,647,874 A | 7/1997 | Hayhurst |
| 5,474,572 A | 12/1995 | Hayhurst | 5,649,963 A | 7/1997 | McDevitt |
| 5,478,344 A | 12/1995 | Stone et al. | 5,658,289 A | 8/1997 | Boucher et al. |
| 5,478,345 A | 12/1995 | Stone et al. | 5,658,299 A | 8/1997 | Hart |
| 5,480,403 A | 1/1996 | Lee et al. | 5,658,313 A | 8/1997 | Thal |
| 5,480,406 A | 1/1996 | Nolan et al. | 5,662,658 A | 9/1997 | Wenstrom, Jr. |
| 5,484,442 A | 1/1996 | Melker et al. | 5,662,663 A | 9/1997 | Shallman |
| 5,486,197 A | 1/1996 | Le et al. | 5,665,112 A | 9/1997 | Thal |
| 5,490,750 A | 2/1996 | Gundy | 5,667,513 A | 9/1997 | Torrie et al. |
| 5,496,331 A | 3/1996 | Xu et al. | 5,671,695 A | 9/1997 | Schroeder |
| 5,496,348 A | 3/1996 | Bonutti | 5,674,224 A | 10/1997 | Howell et al. |
| 5,500,000 A | 3/1996 | Feagin et al. | 5,679,723 A | 10/1997 | Cooper et al. |
| 5,505,736 A | 4/1996 | Reimels et al. | 5,681,352 A | 10/1997 | Clancy, III et al. |
| 5,507,754 A | 4/1996 | Green et al. | 5,683,419 A | 11/1997 | Thal |
| 5,520,691 A | 5/1996 | Branch | 5,688,285 A | 11/1997 | Yamada et al. |
| 5,520,702 A | 5/1996 | Sauer et al. | 5,690,676 A | 11/1997 | DiPoto et al. |
| 5,522,817 A | 6/1996 | Sander et al. | 5,690,678 A | 11/1997 | Johnson |
| 5,522,820 A | 6/1996 | Caspari et al. | 5,695,497 A | 12/1997 | Stahelin et al. |
| 5,522,844 A | 6/1996 | Johnson | 5,697,929 A | 12/1997 | Mellinger |
| 5,522,845 A | 6/1996 | Wenstrom, Jr. | 5,699,657 A | 12/1997 | Paulson |
| 5,522,846 A | 6/1996 | Bonutti | 5,702,397 A | 12/1997 | Goble et al. |
| 5,524,946 A | 6/1996 | Thompson | 5,702,422 A | 12/1997 | Stone |
| 5,527,321 A | 6/1996 | Hinchliffe | 5,702,462 A | 12/1997 | Oberlander |
| 5,527,342 A | 6/1996 | Pietrzak et al. | 5,707,373 A | 1/1998 | Sevrain et al. |
| 5,527,343 A | 6/1996 | Bonutti | 5,713,005 A | 1/1998 | Proebsting |
| 5,534,012 A | 7/1996 | Bonutti | 5,713,904 A | 2/1998 | Errico et al. |
| 5,540,718 A | 7/1996 | Bartlett | 5,713,905 A | 2/1998 | Goble et al. |
| 5,545,178 A | 8/1996 | Kensey et al. | 5,713,921 A | 2/1998 | Bonutti |
| 5,545,228 A | 8/1996 | Kambin | 5,716,359 A | 2/1998 | Ojima et al. |
| 5,549,613 A | 8/1996 | Goble et al. | 5,718,717 A | 2/1998 | Bonutti |
| 5,549,617 A | 8/1996 | Green et al. | 5,720,765 A | 2/1998 | Thal |
| 5,549,630 A | 8/1996 | Bonutti | 5,720,766 A | 2/1998 | Zang et al. |
| 5,549,631 A | 8/1996 | Bonutti | 5,725,549 A | 3/1998 | Lam |
| 5,562,683 A | 10/1996 | Chan | 5,725,556 A | 3/1998 | Moser et al. |
| 5,562,685 A | 10/1996 | Mollenauer et al. | 5,725,581 A | 3/1998 | Br.ang.nemark et al. |
| 5,562,686 A | 10/1996 | Sauer et al. | 5,726,722 A | 3/1998 | Uehara et al. |
| 5,569,305 A | 10/1996 | Bonutti | 5,728,107 A | 3/1998 | Zlock et al. |
| 5,571,090 A | 11/1996 | Sherts | 5,728,109 A | 3/1998 | Schulze et al. |
| 5,571,139 A | 11/1996 | Jenkins, Jr. | 5,728,136 A | 3/1998 | Thal |
| 5,572,655 A | 11/1996 | Tuljapurkar et al. | 5,733,293 A | 3/1998 | Scirica et al. |
| 5,573,286 A | 11/1996 | Rogozinski | 5,733,306 A | 3/1998 | Bonutti |
| 5,573,548 A | 11/1996 | Nazre et al. | 5,733,307 A | 3/1998 | Dinsdale |
| 5,578,057 A | 11/1996 | Wenstrom, Jr. | 5,735,875 A | 4/1998 | Bonutti et al. |
| 5,584,695 A | 12/1996 | Lal Sachdeva et al. | 5,741,259 A | 4/1998 | Chan |
| 5,584,835 A | 12/1996 | Greenfield | 5,741,281 A | 4/1998 | Martin et al. |
| 5,584,836 A | 12/1996 | Ballintyn et al. | 5,743,912 A | 4/1998 | Lahille et al. |
| 5,584,862 A | 12/1996 | Bonutti | 5,746,751 A | 5/1998 | Sherts |
| 5,586,986 A | 12/1996 | Hinchliffe | 5,746,752 A | 5/1998 | Burkhart |
| 5,588,575 A | 12/1996 | Davignon | 5,746,754 A | 5/1998 | Chan |
| 5,591,180 A | 1/1997 | Hinchliffe | 5,749,898 A | 5/1998 | Schulze et al. |
| 5,591,181 A | 1/1997 | Stone et al. | 5,755,729 A | 5/1998 | de la Torre et al. |
| 5,591,207 A | 1/1997 | Coleman | 5,766,176 A | 6/1998 | Duncan |
| 5,593,407 A | 1/1997 | Reis et al. | 5,766,250 A | 6/1998 | Chervitz et al. |
| 5,593,425 A | 1/1997 | Bonutti et al. | 5,769,894 A | 6/1998 | Ferragamo |
| 5,601,557 A | 2/1997 | Hayhurst | 5,769,899 A | 6/1998 | Schwartz et al. |
| 5,601,559 A | 2/1997 | Melker et al. | 5,772,673 A | 6/1998 | Cuny et al. |
| 5,601,571 A | 2/1997 | Moss | 5,776,196 A | 7/1998 | Matsuzaki et al. |
| 5,603,716 A | 2/1997 | Morgan et al. | 5,782,862 A | 7/1998 | Bonutti |
| 5,607,429 A | 3/1997 | Hayano et al. | 5,782,864 A | 7/1998 | Lizardi |
| 5,618,290 A | 4/1997 | Toy et al. | 5,782,866 A | 7/1998 | Wenstrom, Jr. |
| 5,628,756 A | 5/1997 | Barker, Jr. et al. | 5,785,714 A | 7/1998 | Morgan et al. |
| 5,628,766 A | 5/1997 | Johnson | 5,792,142 A | 8/1998 | Galitzer |
| 5,630,824 A | 5/1997 | Hart | 5,792,149 A | 8/1998 | Sherts et al. |
| 5,632,748 A | 5/1997 | Beck, Jr. et al. | 5,796,127 A | 8/1998 | Hayafuji et al. |
| 5,641,256 A | 6/1997 | Gundy | 5,797,928 A | 8/1998 | Kogasaka et al. |
| 5,643,266 A | 7/1997 | Li | 5,800,407 A | 9/1998 | Eldor et al. |
| 5,643,269 A | 7/1997 | Harle et al. | 5,810,824 A | 9/1998 | Chan |
| 5,643,320 A | 7/1997 | Lower et al. | 5,810,848 A | 9/1998 | Hayhurst |
| 5,643,321 A | 7/1997 | McDevitt | 5,814,069 A | 9/1998 | Schulze et al. |
| 5,645,546 A | 7/1997 | Fard | 5,814,070 A | 9/1998 | Borzone et al. |
| 5,645,547 A | 7/1997 | Coleman | 5,814,072 A | 9/1998 | Bonutti |
| 5,645,568 A | 7/1997 | Chervitz et al. | 5,814,073 A | 9/1998 | Bonutti |
| 5,645,588 A | 7/1997 | Graf et al. | 5,823,980 A | 10/1998 | Kopfer |

| | | | | | | |
|---|---|---|---|---|---|---|
| 5,824,011 A | 10/1998 | Stone et al. | | 6,045,571 A | 4/2000 | Hill et al. |
| 5,843,084 A | 12/1998 | Hart et al. | | 6,045,573 A | 4/2000 | Wenstrom, Jr. et al. |
| 5,845,645 A | 12/1998 | Bonutti | | 6,045,574 A | 4/2000 | Thal |
| 5,846,254 A | 12/1998 | Schulze et al. | | 6,047,826 A | 4/2000 | Kalinski et al. |
| 5,848,983 A | 12/1998 | Basaj et al. | | 6,048,343 A | 4/2000 | Mathis et al. |
| 5,860,973 A | 1/1999 | Michelson | | 6,051,006 A | 4/2000 | Shluzas et al. |
| 5,868,740 A | 2/1999 | LeVeen et al. | | 6,053,916 A | 4/2000 | Moore |
| 5,868,789 A | 2/1999 | Huebner | | 6,056,752 A | 5/2000 | Roger et al. |
| 5,871,484 A | 2/1999 | Spievack et al. | | 6,056,772 A | 5/2000 | Bonutti |
| 5,871,486 A | 2/1999 | Huebner et al. | | 6,056,773 A | 5/2000 | Bonutti |
| 5,871,490 A | 2/1999 | Schulze et al. | | 6,059,817 A | 5/2000 | Bonutti et al. |
| 5,885,294 A | 3/1999 | Pedlick et al. | | 6,062,344 A | 5/2000 | Okabe et al. |
| 5,891,168 A | 4/1999 | Thal | | 6,068,648 A | 5/2000 | Cole et al. |
| 5,893,592 A | 4/1999 | Schulze et al. | | 6,074,403 A | 6/2000 | Nord |
| 5,895,395 A | 4/1999 | Yeung | | 6,077,277 A | 6/2000 | Mollenauer et al. |
| 5,897,564 A | 4/1999 | Schulze et al. | | 6,077,292 A | 6/2000 | Bonutti |
| 5,897,574 A | 4/1999 | Bonutti | | 6,086,591 A | 7/2000 | Bojarski |
| 5,899,902 A | 5/1999 | Brown et al. | | 6,086,592 A | 7/2000 | Rosenberg et al. |
| 5,899,938 A | 5/1999 | Sklar et al. | | 6,086,608 A | 7/2000 | Ek et al. |
| 5,908,421 A | 6/1999 | Beger et al. | | 6,096,060 A | 8/2000 | Fitts et al. |
| 5,908,436 A | 6/1999 | Cuschieri et al. | | 6,099,530 A | 8/2000 | Simonian et al. |
| 5,910,148 A | 6/1999 | Reimels et al. | | 6,099,568 A | 8/2000 | Simonian et al. |
| 5,911,721 A | 6/1999 | Nicholson et al. | | 6,106,545 A | 8/2000 | Egan |
| 5,918,604 A | 7/1999 | Whelan | | 6,110,128 A | 8/2000 | Andelin et al. |
| 5,921,986 A | 7/1999 | Bonutti | | 6,117,160 A | 9/2000 | Bonutti |
| 5,925,008 A | 7/1999 | Douglas | | 6,117,162 A | 9/2000 | Schmieding et al. |
| 5,928,267 A | 7/1999 | Bonutti et al. | | 6,123,710 A | 9/2000 | Pinczewski et al. |
| 5,931,838 A | 8/1999 | Vito | | 6,132,433 A | 10/2000 | Whelan |
| 5,931,844 A | 8/1999 | Thompson et al. | | 6,132,437 A | 10/2000 | Omurtag et al. |
| 5,931,869 A | 8/1999 | Boucher et al. | | 6,139,565 A | 10/2000 | Stone et al. |
| 5,935,149 A | 8/1999 | Ek | | RE36,974 E | 11/2000 | Bonutti |
| 5,938,668 A | 8/1999 | Scirica et al. | | 6,143,017 A | 11/2000 | Thal |
| 5,941,439 A | 8/1999 | Kammerer et al. | | 6,146,406 A | 11/2000 | Shluzas et al. |
| 5,941,900 A | 8/1999 | Bonutti | | 6,146,408 A | 11/2000 | Bartlett |
| 5,944,739 A | 8/1999 | Zlock et al. | | 6,149,653 A | 11/2000 | Deslauriers |
| 5,946,783 A | 9/1999 | Plociennik et al. | | 6,149,669 A | 11/2000 | Li |
| 5,947,915 A | 9/1999 | Thibodo, Jr. | | 6,152,928 A | 11/2000 | Wenstrom, Jr. |
| 5,947,982 A | 9/1999 | Duran | | 6,152,934 A | 11/2000 | Harper et al. |
| 5,948,002 A | 9/1999 | Bonutti | | 6,152,936 A | 11/2000 | Christy et al. |
| 5,951,559 A | 9/1999 | Burkhart | | 6,152,949 A | 11/2000 | Bonutti |
| 5,951,560 A | 9/1999 | Simon et al. | | 6,156,039 A | 12/2000 | Thal |
| 5,954,747 A | 9/1999 | Clark | | 6,156,056 A | 12/2000 | Kearns et al. |
| 5,957,953 A | 9/1999 | DiPoto et al. | | 6,159,234 A | 12/2000 | Bonutti et al. |
| 5,961,521 A | 10/1999 | Roger et al. | | 6,165,203 A | 12/2000 | Krebs |
| 5,961,524 A | 10/1999 | Crombie | | 6,168,598 B1 | 1/2001 | Martello |
| 5,964,764 A | 10/1999 | West, Jr. et al. | | 6,168,628 B1 | 1/2001 | Huebner |
| 5,964,767 A | 10/1999 | Tapia et al. | | 6,179,840 B1 | 1/2001 | Bowman |
| 5,964,783 A | 10/1999 | Grafton et al. | | 6,187,025 B1 | 2/2001 | Machek |
| 5,968,045 A | 10/1999 | Frazier | | 6,190,401 B1 | 2/2001 | Green et al. |
| 5,968,047 A | 10/1999 | Reed | | 6,190,411 B1 | 2/2001 | Lo et al. |
| 5,976,125 A | 11/1999 | Graham | | 6,193,754 B1 | 2/2001 | Seedhom et al. |
| 5,976,127 A | 11/1999 | Lax | | 6,200,329 B1 | 3/2001 | Fung et al. |
| 5,980,524 A | 11/1999 | Justin et al. | | 6,200,330 B1 | 3/2001 | Benderev et al. |
| 5,980,558 A | 11/1999 | Wiley | | 6,203,565 B1 | 3/2001 | Bonutti et al. |
| 5,980,559 A | 11/1999 | Bonutti | | 6,203,572 B1 | 3/2001 | Johnson et al. |
| 5,989,252 A | 11/1999 | Fumex et al. | | 6,206,883 B1 | 3/2001 | Tunc |
| 5,989,256 A | 11/1999 | Kuslich et al. | | 6,210,376 B1 | 4/2001 | Grayson |
| 5,989,282 A | 11/1999 | Bonutti | | 6,214,012 B1 | 4/2001 | Karpman et al. |
| 5,993,452 A | 11/1999 | Vandewalle | | 6,221,107 B1 | 4/2001 | Steiner et al. |
| 5,997,542 A | 12/1999 | Burke | | 6,228,096 B1 | 5/2001 | Marchand |
| 5,997,552 A | 12/1999 | Person et al. | | 6,231,592 B1 | 5/2001 | Bonutti et al. |
| 6,001,100 A | 12/1999 | Sherman et al. | | 6,235,057 B1 | 5/2001 | Roger et al. |
| 6,007,567 A | 12/1999 | Bonutti | | 6,238,395 B1 | 5/2001 | Bonutti |
| 6,010,525 A | 1/2000 | Bonutti et al. | | 6,241,734 B1 | 6/2001 | Scribner et al. |
| 6,016,727 A | 1/2000 | Morgan | | 6,241,747 B1 | 6/2001 | Ruff |
| 6,022,352 A | 2/2000 | Vandewalle | | 6,241,771 B1 | 6/2001 | Gresser et al. |
| 6,022,373 A | 2/2000 | Li | | 6,245,081 B1 | 6/2001 | Bowman et al. |
| 6,024,758 A | 2/2000 | Thal | | 6,258,091 B1 | 7/2001 | Sevrain et al. |
| 6,027,523 A | 2/2000 | Schmieding | | 6,267,766 B1 | 7/2001 | Burkhart |
| 6,033,430 A | 3/2000 | Bonutti | | 6,269,716 B1 | 8/2001 | Amis |
| 6,039,753 A | 3/2000 | Meislin | | 6,270,518 B1 | 8/2001 | Pedlick et al. |
| 6,042,601 A | 3/2000 | Smith | | 6,273,890 B1 | 8/2001 | Frazier |
| 6,045,551 A | 4/2000 | Bonutti | | 6,283,973 B1 | 9/2001 | Hubbard et al. |

| | | | | | |
|---|---|---|---|---|---|
| 6,283,996 B1 | 9/2001 | Chervitz et al. | 6,551,330 B1 | 4/2003 | Bain et al. |
| 6,287,325 B1 | 9/2001 | Bonutti | 6,551,343 B1 | 4/2003 | Tormala et al. |
| 6,293,961 B2 | 9/2001 | Schwartz et al. | 6,553,802 B1 | 4/2003 | Jacob et al. |
| 6,296,659 B1 | 10/2001 | Foerster | 6,554,830 B1 | 4/2003 | Chappius |
| 6,299,615 B1 | 10/2001 | Huebner | 6,554,852 B1 | 4/2003 | Oberlander |
| 6,302,888 B1 | 10/2001 | Mellinger et al. | 6,554,862 B2 | 4/2003 | Hays et al. |
| 6,306,156 B1 | 10/2001 | Clark | 6,562,071 B2 | 5/2003 | Jarvinen et al. |
| 6,306,159 B1 | 10/2001 | Schwartz et al. | 6,565,572 B2 | 5/2003 | Chappius |
| 6,309,405 B1 | 10/2001 | Bonutti | 6,565,573 B1 | 5/2003 | Ferrante et al. |
| 6,312,448 B1 | 11/2001 | Bonutti | 6,569,186 B1 | 5/2003 | Winters et al. |
| 6,319,271 B1 | 11/2001 | Schwartz et al. | 6,569,187 B1 | 5/2003 | Bonutti et al. |
| 6,328,758 B1 * | 12/2001 | Tornier et al. ............... 606/232 | 6,572,635 B1 | 6/2003 | Bonutti |
| 6,342,060 B1 * | 1/2002 | Adams ....................... 606/151 | 6,575,925 B1 | 6/2003 | Noble |
| 6,343,531 B2 | 2/2002 | Amis | 6,579,295 B1 | 6/2003 | Supinski |
| 6,364,897 B1 | 4/2002 | Bonutti | 6,582,453 B1 | 6/2003 | Tran et al. |
| 6,368,322 B1 | 4/2002 | Luks et al. | 6,585,730 B1 | 7/2003 | Foerster |
| 6,368,326 B1 | 4/2002 | Dakin et al. | 6,585,740 B2 | 7/2003 | Schlapfer et al. |
| 6,368,343 B1 | 4/2002 | Bonutti et al. | 6,585,750 B2 | 7/2003 | Bonutti et al. |
| 6,371,124 B1 | 4/2002 | Whelan | 6,589,245 B1 | 7/2003 | Weiler et al. |
| 6,379,361 B1 | 4/2002 | Beck, Jr. et al. | 6,589,246 B1 | 7/2003 | Hack et al. |
| 6,383,190 B1 | 5/2002 | Preissman | 6,592,609 B1 | 7/2003 | Bonutti |
| 6,383,199 B2 | 5/2002 | Carter et al. | 6,595,911 B2 | 7/2003 | LoVuolo |
| 6,387,113 B1 | 5/2002 | Hawkins et al. | 6,599,289 B1 | 7/2003 | Bojarski et al. |
| 6,387,129 B2 | 5/2002 | Rieser et al. | 6,605,096 B1 | 8/2003 | Ritchart |
| 6,398,785 B2 | 6/2002 | Carchidi et al. | 6,607,548 B2 | 8/2003 | Pohjonen et al. |
| 6,406,479 B1 * | 6/2002 | Justin et al. ................. 606/104 | 6,613,018 B2 | 9/2003 | Bagga et al. |
| 6,409,743 B1 | 6/2002 | Fenton, Jr. | 6,616,694 B1 | 9/2003 | Hart |
| 6,413,260 B1 | 7/2002 | Berrevoets et al. | 6,620,166 B1 | 9/2003 | Wenstrom, Jr. et al. |
| 6,423,088 B1 | 7/2002 | Fenton, Jr. | 6,620,185 B1 | 9/2003 | Harvie et al. |
| 6,428,562 B2 | 8/2002 | Bonutti | 6,620,195 B2 | 9/2003 | Goble et al. |
| 6,432,123 B2 | 8/2002 | Schwartz et al. | 6,620,329 B2 | 9/2003 | Rosen et al. |
| 6,436,124 B1 | 8/2002 | Anderson et al. | 6,620,349 B1 | 9/2003 | Lopez |
| 6,440,134 B1 | 8/2002 | Zaccherotti et al. | 6,623,492 B1 | 9/2003 | Berube et al. |
| 6,440,136 B1 | 8/2002 | Gambale et al. | 6,623,524 B2 | 9/2003 | Schmieding |
| 6,447,516 B1 | 9/2002 | Bonutti | 6,626,910 B1 | 9/2003 | Hugues et al. |
| 6,451,030 B2 | 9/2002 | Li et al. | 6,626,919 B1 | 9/2003 | Swanstrom |
| 6,454,768 B1 | 9/2002 | Jackson | 6,629,977 B1 | 10/2003 | Wolf |
| 6,458,134 B1 | 10/2002 | Songer et al. | 6,635,073 B2 | 10/2003 | Bonutti |
| 6,461,373 B2 | 10/2002 | Wyman et al. | 6,638,279 B2 | 10/2003 | Bonutti |
| 6,464,713 B2 | 10/2002 | Bonutti | 6,641,596 B1 | 11/2003 | Lizardi |
| 6,468,293 B2 | 10/2002 | Bonutti et al. | 6,641,597 B2 | 11/2003 | Burkhart et al. |
| 6,471,707 B1 | 10/2002 | Miller et al. | 6,645,227 B2 | 11/2003 | Fallin et al. |
| 6,475,230 B1 | 11/2002 | Bonutti et al. | 6,652,562 B2 | 11/2003 | Collier et al. |
| 6,482,210 B1 | 11/2002 | Skiba et al. | 6,652,563 B2 | 11/2003 | Dreyfuss |
| 6,485,504 B1 | 11/2002 | Johnson et al. | 6,656,182 B1 | 12/2003 | Hayhurst |
| 6,497,901 B1 | 12/2002 | Royer | 6,656,183 B2 | 12/2003 | Colleran et al. |
| 6,500,184 B1 | 12/2002 | Chan et al. | 6,658,182 B1 | 12/2003 | Gonthier et al. |
| 6,500,195 B2 | 12/2002 | Bonutti | 6,660,008 B1 | 12/2003 | Foerster et al. |
| RE37,963 E | 1/2003 | Thal | 6,660,022 B1 | 12/2003 | Li et al. |
| 6,503,267 B2 | 1/2003 | Bonutti et al. | 6,663,634 B2 | 12/2003 | Ahrens et al. |
| 6,508,820 B2 | 1/2003 | Bales | 6,663,656 B2 | 12/2003 | Schmieding et al. |
| 6,508,821 B1 | 1/2003 | Schwartz et al. | 6,666,868 B2 | 12/2003 | Fallin |
| 6,508,830 B2 | 1/2003 | Steiner | 6,682,549 B2 | 1/2004 | Bartlett |
| 6,511,498 B1 | 1/2003 | Fumex et al. | 6,685,728 B2 | 2/2004 | Sinnott et al. |
| 6,511,499 B2 | 1/2003 | Schmieding et al. | 6,689,137 B2 | 2/2004 | Reed |
| 6,517,542 B1 | 2/2003 | Papay et al. | 6,689,154 B2 | 2/2004 | Bartlett |
| 6,517,552 B1 | 2/2003 | Nord et al. | 6,692,499 B2 | 2/2004 | Tormala et al. |
| 6,517,578 B2 | 2/2003 | Hein et al. | 6,712,849 B2 | 3/2004 | Re et al. |
| 6,517,579 B1 | 2/2003 | Paulos et al. | 6,716,224 B2 | 4/2004 | Singhatat |
| 6,520,964 B2 | 2/2003 | Tallarida et al. | 6,716,957 B2 | 4/2004 | Tunc |
| 6,520,980 B1 | 2/2003 | Foerster | 6,730,092 B2 | 5/2004 | Songer |
| 6,524,317 B1 | 2/2003 | Ritchart et al. | 6,730,124 B2 | 5/2004 | Steiner |
| 6,527,777 B2 | 3/2003 | Justin | 6,736,799 B1 | 5/2004 | Erbe et al. |
| 6,527,794 B1 | 3/2003 | McDevitt et al. | 6,746,483 B1 | 6/2004 | Bojarski et al. |
| 6,527,795 B1 | 3/2003 | Lizardi | 6,755,836 B1 | 6/2004 | Lewis |
| 6,533,795 B1 | 3/2003 | Tran et al. | 6,761,739 B2 | 7/2004 | Shepard |
| 6,533,802 B2 | 3/2003 | Bojarski et al. | 6,767,037 B2 | 7/2004 | Wenstrom, Jr. |
| 6,537,319 B2 | 3/2003 | Whelan | 6,770,076 B2 | 8/2004 | Foerster |
| 6,540,750 B2 | 4/2003 | Burkhart | 6,770,084 B1 | 8/2004 | Bain et al. |
| 6,540,770 B1 | 4/2003 | Tornier et al. | 6,773,450 B2 | 8/2004 | Leung et al. |
| 6,544,281 B2 | 4/2003 | ElAttrache et al. | 6,780,190 B2 | 8/2004 | Maroney |
| 6,547,564 B1 | 4/2003 | Hansson et al. | 6,780,198 B1 | 8/2004 | Gregoire et al. |
| 6,547,800 B2 | 4/2003 | Foerster et al. | 6,802,862 B1 | 10/2004 | Roger et al. |

| | | | |
|---|---|---|---|
| 6,808,502 B2 | 10/2004 | Nguyen et al. | |
| 6,808,526 B1 | 10/2004 | Magerl et al. | |
| 6,814,741 B2 | 11/2004 | Bowman et al. | |
| 6,830,572 B2 | 12/2004 | McDevitt et al. | |
| 6,833,005 B1 | 12/2004 | Mantas et al. | |
| 6,840,953 B2 | 1/2005 | Martinek | |
| 6,860,885 B2 | 3/2005 | Bonutti | |
| 6,863,671 B1 | 3/2005 | Strobel et al. | |
| 6,872,040 B2 | 3/2005 | Deeg et al. | |
| 6,875,216 B2 | 4/2005 | Wolf | |
| 6,884,249 B2 | 4/2005 | May et al. | |
| 6,887,259 B2 | 5/2005 | Lizardi | |
| 6,890,354 B2 | 5/2005 | Steiner et al. | |
| 6,893,448 B2 | 5/2005 | O'Quinn et al. | |
| 6,896,686 B2 | 5/2005 | Weber | |
| 6,899,722 B2 | 5/2005 | Bonutti | |
| 6,902,573 B2 | 6/2005 | Strobel et al. | |
| 6,908,466 B1 | 6/2005 | Bonutti et al. | |
| 6,916,292 B2 | 7/2005 | Morawski et al. | |
| 6,916,321 B2 | 7/2005 | TenHuisen et al. | |
| 6,921,402 B2 | 7/2005 | Contiliano et al. | |
| 6,923,823 B1 | 8/2005 | Bartlett et al. | |
| 6,923,824 B2 | 8/2005 | Morgan et al. | |
| 6,951,565 B2 | 10/2005 | Keane et al. | |
| 6,972,027 B2 | 12/2005 | Fallin et al. | |
| 6,980,903 B2 | 12/2005 | Daniels et al. | |
| 6,986,781 B2 | 1/2006 | Smith | |
| 6,989,034 B2 | 1/2006 | Hammer et al. | |
| 7,066,942 B2 | 6/2006 | Treace | |
| 7,066,944 B2 | 6/2006 | Laufer et al. | |
| 7,105,010 B2 | 9/2006 | Hart et al. | |
| 7,112,221 B2 | 9/2006 | Harris | |
| 7,118,583 B2 | 10/2006 | O'Quinn et al. | |
| 7,137,996 B2 | 11/2006 | Steiner et al. | |
| 7,141,066 B2 | 11/2006 | Steiner et al. | |
| 7,153,307 B2 | 12/2006 | Scribner et al. | |
| 7,153,312 B1 | 12/2006 | Torrie et al. | |
| 7,201,722 B2 | 4/2007 | Krueger | |
| 7,261,716 B2 | 8/2007 | Strobel et al. | |
| 7,264,634 B2 | 9/2007 | Schmieding | |
| 7,285,124 B2 | 10/2007 | Foerster | |
| 7,306,417 B2 | 12/2007 | Dorstewitz | |
| 7,390,332 B2 | 6/2008 | Selvitelli et al. | |
| 7,608,098 B1 | 10/2009 | Stone et al. | |
| 7,615,076 B2 * | 11/2009 | Cauthen et al. | 623/17.11 |
| 7,651,509 B2 * | 1/2010 | Bojarski et al. | 606/139 |
| 7,678,123 B2 * | 3/2010 | Chanduszko | 606/151 |
| 7,695,493 B2 * | 4/2010 | Saadat et al. | 606/215 |
| 7,736,379 B2 * | 6/2010 | Ewers et al. | 606/232 |
| 7,758,594 B2 * | 7/2010 | Lamson et al. | 606/139 |
| 2001/0014825 A1 | 8/2001 | Burke et al. | |
| 2001/0037131 A1 | 11/2001 | Schmieding et al. | |
| 2001/0037153 A1 | 11/2001 | Rockwood et al. | |
| 2001/0041916 A1 | 11/2001 | Bonutti | |
| 2001/0041937 A1 | 11/2001 | Rieser et al. | |
| 2001/0041938 A1 | 11/2001 | Hein | |
| 2001/0044639 A1 | 11/2001 | Levinson | |
| 2001/0047206 A1 | 11/2001 | Sklar et al. | |
| 2001/0051816 A1 | 12/2001 | Enzerink et al. | |
| 2001/0053934 A1 | 12/2001 | Schmieding | |
| 2002/0001964 A1 | 1/2002 | Choi | |
| 2002/0004669 A1 | 1/2002 | Bartlett | |
| 2002/0007182 A1 | 1/2002 | Kim | |
| 2002/0010513 A1 | 1/2002 | Schmieding | |
| 2002/0013608 A1 | 1/2002 | ElAttrache et al. | |
| 2002/0019649 A1 | 2/2002 | Sikora et al. | |
| 2002/0055780 A1 | 5/2002 | Sklar | |
| 2002/0058966 A1 | 5/2002 | Tormala et al. | |
| 2002/0099411 A1 | 7/2002 | Bartlett | |
| 2002/0111653 A1 | 8/2002 | Foerster | |
| 2002/0120270 A1 | 8/2002 | Trieu et al. | |
| 2002/0120292 A1 | 8/2002 | Morgan | |
| 2002/0123752 A1 | 9/2002 | Schultheiss et al. | |
| 2002/0128684 A1 | 9/2002 | Foerster | |
| 2002/0147463 A1 | 10/2002 | Martinek | |
| 2002/0161401 A1 | 10/2002 | Steiner | |
| 2002/0161439 A1 | 10/2002 | Strobel et al. | |
| 2002/0169452 A1 | 11/2002 | Tormala et al. | |
| 2002/0169477 A1 | 11/2002 | Demopulos et al. | |
| 2002/0169478 A1 | 11/2002 | Schwartz et al. | |
| 2002/0173788 A1 | 11/2002 | Bojarski et al. | |
| 2002/0188298 A1 | 12/2002 | Chan | |
| 2003/0023268 A1 | 1/2003 | Lizardi | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0065391 A1 | 4/2003 | Re et al. | |
| 2003/0078603 A1 * | 4/2003 | Schaller et al. | 606/151 |
| 2003/0078617 A1 | 4/2003 | Schwartz et al. | |
| 2003/0083662 A1 | 5/2003 | Middleton | |
| 2003/0088251 A1 | 5/2003 | Braun et al. | |
| 2003/0088272 A1 | 5/2003 | Smith | |
| 2003/0105477 A1 | 6/2003 | Schwartz et al. | |
| 2003/0120309 A1 | 6/2003 | Colleran et al. | |
| 2003/0130694 A1 | 7/2003 | Bojarski et al. | |
| 2003/0135214 A1 | 7/2003 | Fetto et al. | |
| 2003/0135239 A1 | 7/2003 | Gabriel et al. | |
| 2003/0135963 A1 | 7/2003 | Holbrook et al. | |
| 2003/0152522 A1 | 8/2003 | Miller et al. | |
| 2003/0167072 A1 | 9/2003 | Oberlander | |
| 2003/0167090 A1 | 9/2003 | Chervitz et al. | |
| 2003/0171811 A1 | 9/2003 | Steiner et al. | |
| 2003/0176865 A1 | 9/2003 | Supinski | |
| 2003/0176919 A1 | 9/2003 | Schmieding | |
| 2003/0181925 A1 | 9/2003 | Bain et al. | |
| 2003/0195528 A1 | 10/2003 | Ritchart | |
| 2003/0220660 A1 | 11/2003 | Kortenbach et al. | |
| 2003/0225459 A1 | 12/2003 | Hammer et al. | |
| 2004/0002734 A1 | 1/2004 | Fallin et al. | |
| 2004/0006345 A1 | 1/2004 | Vlahos et al. | |
| 2004/0006346 A1 | 1/2004 | Holmen et al. | |
| 2004/0015171 A1 | 1/2004 | Bojarski et al. | |
| 2004/0015172 A1 | 1/2004 | Biedermann et al. | |
| 2004/0024456 A1 | 2/2004 | Brown et al. | |
| 2004/0087981 A1 | 5/2004 | Berube et al. | |
| 2004/0092936 A1 | 5/2004 | Miller et al. | |
| 2004/0098051 A1 | 5/2004 | Fallin et al. | |
| 2004/0111117 A1 | 6/2004 | Colleran et al. | |
| 2004/0122431 A1 | 6/2004 | Biedermann et al. | |
| 2004/0133211 A1 | 7/2004 | Raskin et al. | |
| 2004/0138664 A1 | 7/2004 | Bowman | |
| 2004/0138683 A1 | 7/2004 | Shelton et al. | |
| 2004/0138704 A1 | 7/2004 | Gambale et al. | |
| 2004/0138706 A1 | 7/2004 | Abrams et al. | |
| 2004/0143344 A1 | 7/2004 | Malaviya et al. | |
| 2004/0153103 A1 | 8/2004 | Schwartz et al. | |
| 2004/0153153 A1 | 8/2004 | Elson et al. | |
| 2004/0162579 A1 | 8/2004 | Foerster | |
| 2004/0166169 A1 | 8/2004 | Malaviya et al. | |
| 2004/0182968 A1 | 9/2004 | Gentry | |
| 2004/0220574 A1 | 11/2004 | Pelo et al. | |
| 2004/0225292 A1 | 11/2004 | Sasso et al. | |
| 2004/0236353 A1 | 11/2004 | Bain et al. | |
| 2004/0243139 A1 | 12/2004 | Lewis et al. | |
| 2004/0243178 A1 | 12/2004 | Haut et al. | |
| 2004/0249394 A1 | 12/2004 | Morris et al. | |
| 2004/0267164 A1 | 12/2004 | Rhodes et al. | |
| 2004/0267265 A1 | 12/2004 | Kyle | |
| 2004/0267270 A1 | 12/2004 | Jacobs et al. | |
| 2004/0267276 A1 | 12/2004 | Camino et al. | |
| 2004/0267277 A1 | 12/2004 | Zannis et al. | |
| 2004/0267304 A1 | 12/2004 | Zannis et al. | |
| 2005/0027307 A1 | 2/2005 | Schwartz et al. | |
| 2005/0033363 A1 | 2/2005 | Bojarski et al. | |

| | | | | | |
|---|---|---|---|---|---|
| 2005/0038426 A1 | 2/2005 | Chan | 2009/0318961 A1 | 12/2009 | Stone et al. |
| 2005/0055027 A1* | 3/2005 | Yeung et al. .................. 606/75 | | | |
| 2005/0064042 A1 | 3/2005 | Vunjak-Novakovic et al. | FOREIGN PATENT DOCUMENTS | | |
| 2005/0074495 A1 | 4/2005 | Schwartz et al. | | | |
| 2005/0090828 A1 | 4/2005 | Alford | AU | 440266 | 10/1967 |
| 2005/0096696 A1 | 5/2005 | Forsberg | AU | 2223767 | 11/1968 |
| 2005/0096697 A1 | 5/2005 | Forsberg et al. | AU | 5028569 | 8/1970 |
| 2005/0107828 A1 | 5/2005 | Reese | AU | 5850469 | 1/1971 |
| 2005/0119531 A1 | 6/2005 | Sharratt | AU | 5963869 | 2/1971 |
| 2005/0125073 A1 | 6/2005 | Orban et al. | AU | 1505470 | 11/1971 |
| 2005/0137600 A1 | 6/2005 | Jacobs et al. | AU | 3615171 | 5/1973 |
| 2005/0149033 A1 | 7/2005 | McGuire et al. | AU | 7110887 | 10/1987 |
| 2005/0159812 A1 | 7/2005 | Dinger et al. | AU | 639410 | 11/1989 |
| 2005/0165416 A1 | 7/2005 | Bojarski et al. | AU | 651929 | 8/1994 |
| 2005/0165482 A1 | 7/2005 | Goldhahn et al. | DE | 2529669 | 3/1976 |
| 2005/0203620 A1 | 9/2005 | Steiner et al. | DE | 2747312 | 4/1979 |
| 2005/0222618 A1 | 10/2005 | Dreyfuss et al. | DE | 2818254 | 10/1979 |
| 2005/0222619 A1 | 10/2005 | Dreyfuss et al. | DE | 2919009 | 11/1979 |
| 2005/0228448 A1 | 10/2005 | Li | DE | 3027138 | 12/1981 |
| 2005/0267479 A1 | 12/2005 | Morgan et al. | DE | 3225620 | 2/1983 |
| 2005/0277961 A1 | 12/2005 | Stone et al. | DE | 3136083 | 3/1983 |
| 2005/0283040 A1* | 12/2005 | Greenhalgh .................. 600/30 | DE | 233303 | 2/1986 |
| 2005/0283156 A1 | 12/2005 | Schmieding et al. | DE | 4127550 | 2/1993 |
| 2005/0283158 A1 | 12/2005 | West | DE | 4302397 | 7/1993 |
| 2005/0283192 A1* | 12/2005 | Torrie et al. .................. 606/228 | DE | 29621340 | 5/1998 |
| 2006/0030948 A1 | 2/2006 | Manrique et al. | DE | 19841252 | 3/2000 |
| 2006/0036265 A1 | 2/2006 | Dant | EP | 0108912 | 5/1984 |
| 2006/0064126 A1 | 3/2006 | Fallin et al. | EP | 0129422 | 12/1984 |
| 2006/0069334 A1 | 3/2006 | Moskowitz | EP | 0129442 | 12/1984 |
| 2006/0084943 A1 | 4/2006 | Rosenman et al. | EP | 0172130 | 2/1986 |
| 2006/0100627 A1 | 5/2006 | Stone et al. | EP | 0241240 | 10/1987 |
| 2006/0121084 A1 | 6/2006 | Borden et al. | EP | 0241792 | 10/1987 |
| 2006/0135958 A1 | 6/2006 | Marissen et al. | EP | 0260970 | 3/1988 |
| 2006/0167482 A1 | 7/2006 | Swain et al. | EP | 0270704 | 6/1988 |
| 2006/0178680 A1 | 8/2006 | Nelson et al. | EP | 0282789 | 9/1988 |
| 2006/0189993 A1 | 8/2006 | Stone | EP | 0315371 | 5/1989 |
| 2006/0190042 A1 | 8/2006 | Stone et al. | EP | 0317406 | 5/1989 |
| 2006/0229671 A1 | 10/2006 | Steiner et al. | EP | 0340159 | 11/1989 |
| 2006/0247642 A1 | 11/2006 | Stone et al. | EP | 0346183 | 12/1989 |
| 2006/0271192 A1 | 11/2006 | Olsen et al. | EP | 0349173 | 1/1990 |
| 2006/0280768 A1 | 12/2006 | Hwang et al. | EP | 0374088 | 6/1990 |
| 2006/0282085 A1 | 12/2006 | Stone et al. | EP | 0409364 | 1/1991 |
| 2006/0293709 A1 | 12/2006 | Bojarski et al. | EP | 0415915 | 3/1991 |
| 2007/0016305 A1 | 1/2007 | Chudik | EP | 0440991 | 8/1991 |
| 2007/0055255 A1 | 3/2007 | Siegel | EP | 0441065 | 8/1991 |
| 2007/0060922 A1 | 3/2007 | Dreyfuss | EP | 0451932 | 10/1991 |
| 2007/0067025 A1* | 3/2007 | Schwartz .................. 623/1.39 | EP | 0464480 | 1/1992 |
| 2007/0073307 A1 | 3/2007 | Scribner et al. | EP | 0490417 | 6/1992 |
| 2007/0078435 A1 | 4/2007 | Stone et al. | EP | 0497079 | 8/1992 |
| 2007/0083236 A1 | 4/2007 | Sikora et al. | EP | 0502509 | 9/1992 |
| 2007/0093847 A1 | 4/2007 | Scribner et al. | EP | 0502698 | 9/1992 |
| 2007/0142838 A1 | 6/2007 | Jordan | EP | 520177 | 12/1992 |
| 2007/0185532 A1 | 8/2007 | Stone et al. | EP | 0546726 | 6/1993 |
| 2007/0239209 A1 | 10/2007 | Fallman | EP | 0574707 | 12/1993 |
| 2008/0027446 A1 | 1/2008 | Stone et al. | EP | 0582514 | 2/1994 |
| 2008/0065114 A1 | 3/2008 | Stone et al. | EP | 0591991 | 4/1994 |
| 2008/0082127 A1 | 4/2008 | Stone et al. | EP | 0598219 | 5/1994 |
| 2008/0082128 A1 | 4/2008 | Stone | EP | 0627203 | 12/1994 |
| 2008/0132932 A1 | 6/2008 | Hoeppner et al. | EP | 0651979 | 5/1995 |
| 2008/0140092 A1 | 6/2008 | Stone et al. | EP | 0669110 | 8/1995 |
| 2008/0140093 A1 | 6/2008 | Stone et al. | EP | 0686373 | 12/1995 |
| 2008/0161852 A1 | 7/2008 | Kaiser et al. | EP | 0702933 | 3/1996 |
| 2008/0255613 A1 | 10/2008 | Kaiser et al. | EP | 0775473 | 5/1997 |
| 2008/0268064 A1 | 10/2008 | Woodell-May | EP | 0913123 | 5/1999 |
| 2008/0269674 A1 | 10/2008 | Stone | EP | 0913131 | 5/1999 |
| 2008/0312689 A1 | 12/2008 | Denham et al. | EP | 99121106 | 10/1999 |
| 2009/0054928 A1 | 2/2009 | Denham et al. | EP | 991210527 | 10/1999 |
| 2009/0062854 A1 | 3/2009 | Kaiser et al. | EP | 0995409 | 4/2000 |
| 2009/0082805 A1 | 3/2009 | Kaiser et al. | EP | 1013229 | 6/2000 |
| 2009/0192468 A1 | 7/2009 | Stone | EP | 1093773 | 4/2001 |
| 2009/0306711 A1 | 12/2009 | Stone et al. | EP | 1093774 | 4/2001 |
| 2009/0312776 A1 | 12/2009 | Kaiser et al. | EP | 1555945 | 7/2005 |
| | | | FR | 2622790 | 5/1989 |

| | | |
|---|---|---|
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03071962 | 9/2003 |
| WO | WO-03077772 | 9/2003 |
| WO | WO-2005104992 | 11/2005 |

OTHER PUBLICATIONS

Arthrotek, A Biomet Company; Knees; Sure fire Hybrid Meniscal Device.
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Mark D. Miller et al.; "Pitfalls Associated with FasT-Fix Meniscal Repair," Arthroscopy: The Journal of Arthroscopic and Related Surgery, vol. 18, No. 8 (Oct. 2002): pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
"EZ Loc Femoral Fixation Device," copyright 2005 Arthrotek, Inc. (8 sheets).
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
Bio-Intrafix (TCP/PLA & Intrafix, Tibial Soft Tissue Fasteners, by DePuy Mitek, 6 sheets, (date unknown).
Lawhorn, M.D., Keith, MaxFire™ Meniscal Repair Device with Zip Loop™ Technology, Biomet Sports Medicine, Feb. 29, 2008.
ToggleLoc™ Femoral Fixation Device, Arthrotek, Mar. 31, 2006.
"Do your next distal tendon repair with . . . The Lubbers Technique", Teno Fix® brochure, 2003 (2 pages) Ortheon® Medical.
"Make your next tendon repair an open-and-shut case. The Teno Fix® Tendon Repair System", Teno Fix® brochure, 2003 (2 pages) Ortheon® Medical.
US 6,238,418, 05/2001, Schwartz et al. (withdrawn)

\* cited by examiner

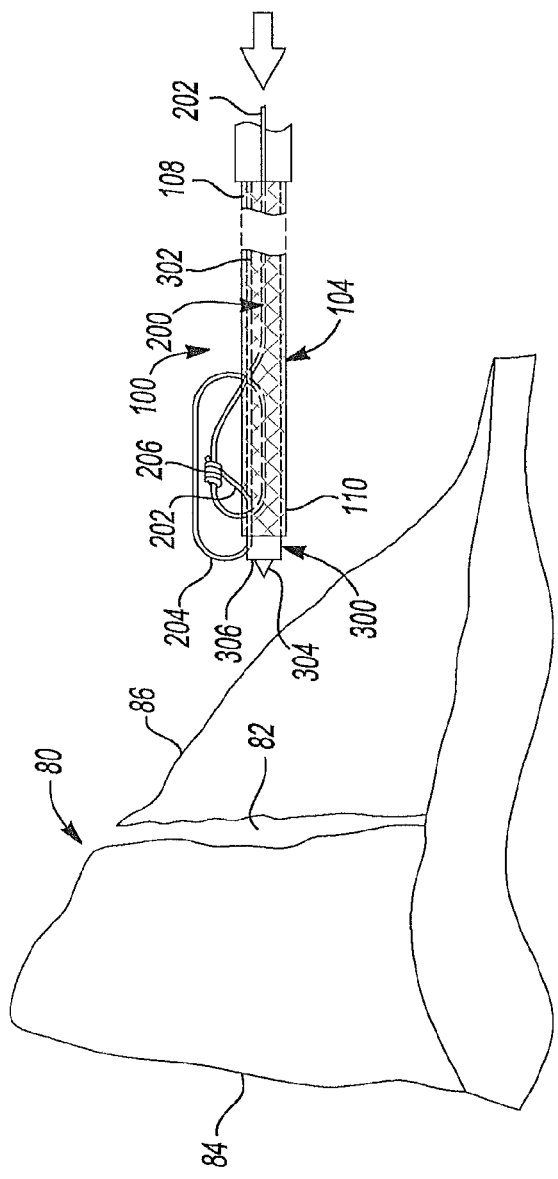
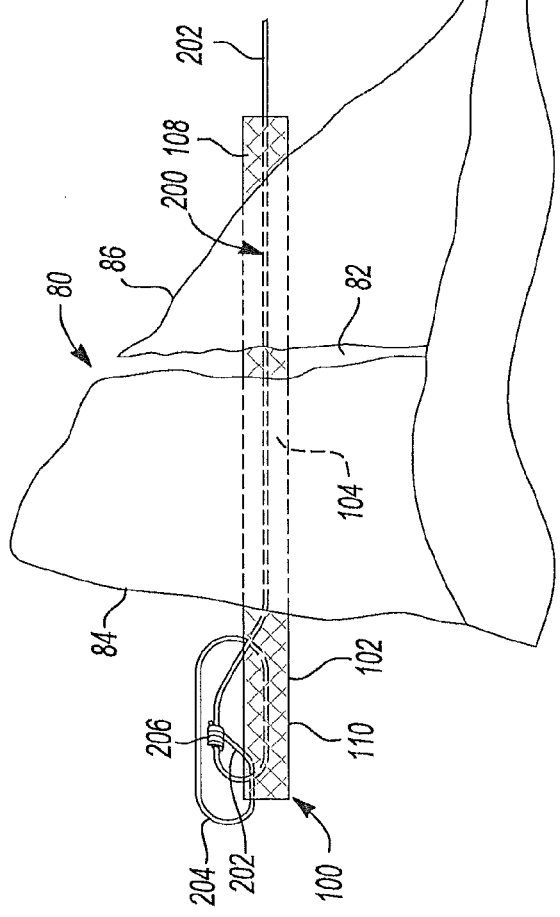
Fig-2A
Fig-2B

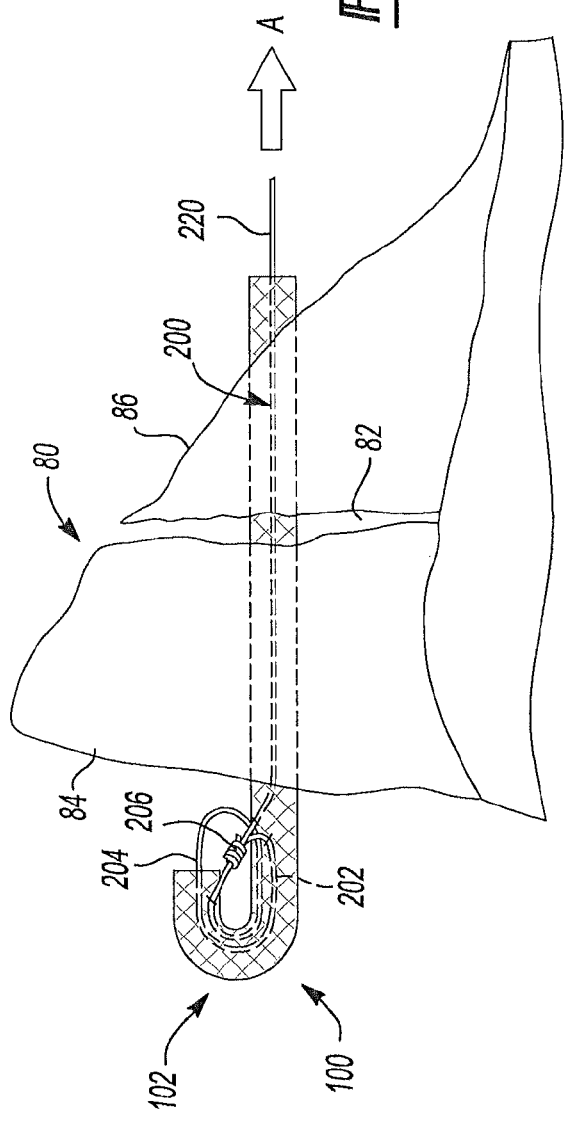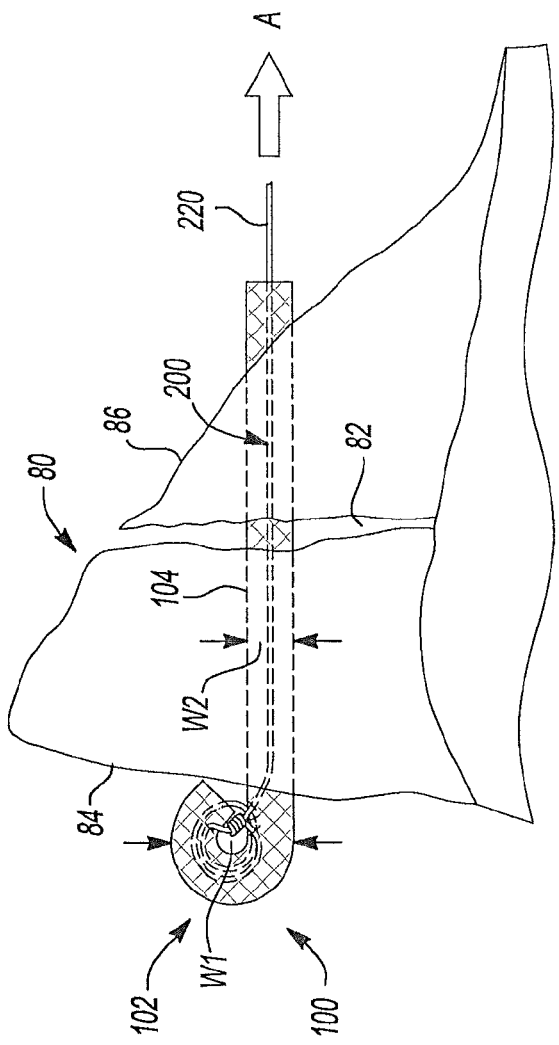

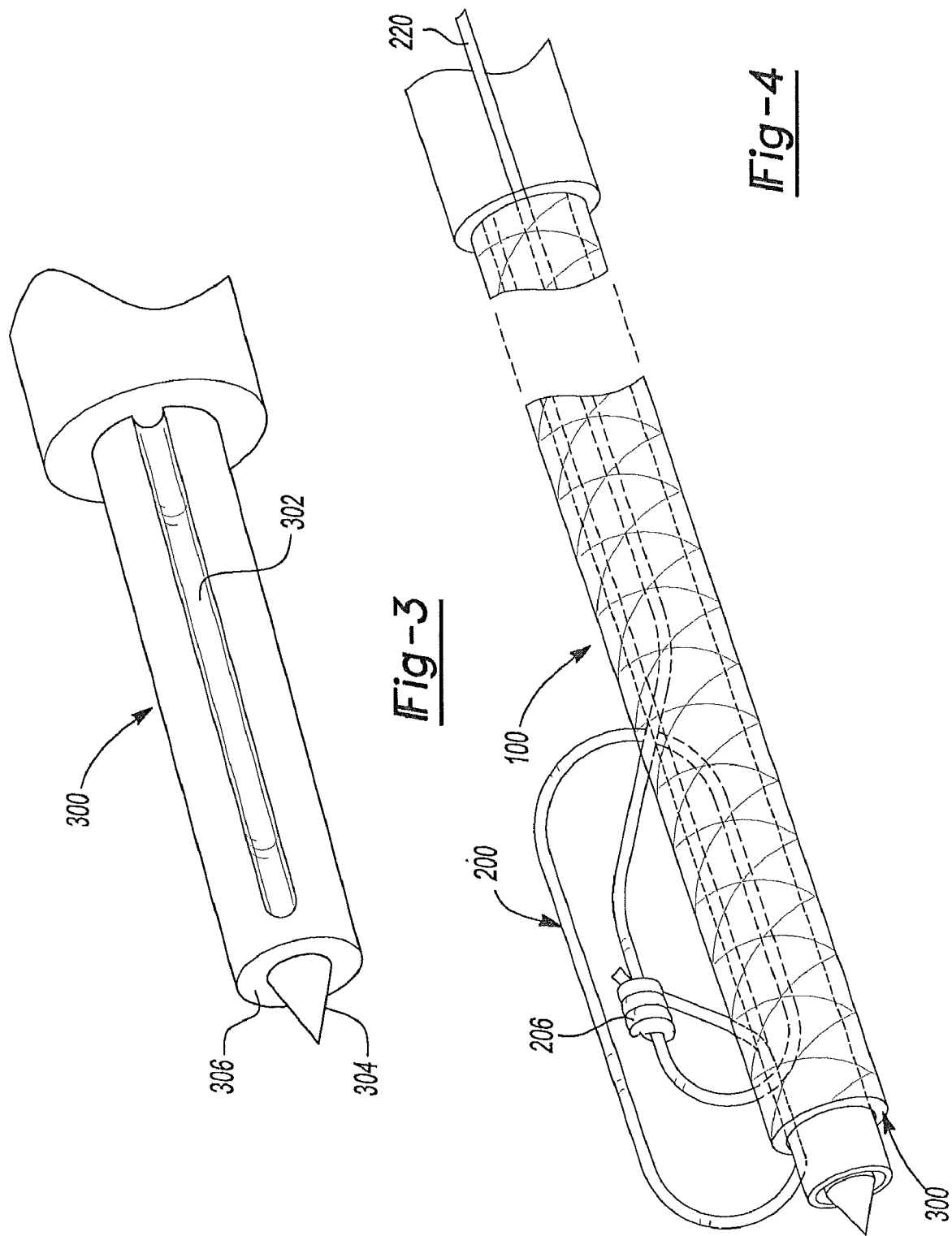

SOFT TISSUE REPAIR AND CONDUIT DEVICE

CROSS-REFERENCE TO RELATED APPLICATIONS

This application is a continuation-in-part of U.S. patent application Ser. No. 11/347,661 filed Feb. 2, 2006 and a continuation-in-part Ser. No. 11/408,282 filed on Apr. 20, 2006. This application claims the benefit of U.S. Provisional Application No. 60/885,062, filed on Jan. 16, 2007, and U.S. Provisional Application No. 60/885,057, filed on Jan. 16, 2007. The disclosures of the above applications are incorporated herein by reference.

INTRODUCTION

Tears caused by trauma or disease in soft tissue, such as cartilage, ligament, or muscle, can be repaired by suturing and/or use of various fixation devices. Various tissue fixation devices have been developed for facilitating suturing and are effective for their intended purposes.

The present teachings provide a soft tissue repair and conduit device for repairing soft tissue defects and providing a conduit for facilitating healing and promoting soft tissue vascularity.

SUMMARY

The present teachings provide a soft tissue repair method. The method includes providing a flaccid tubular member having a longitudinal bore and first and second ends, the tubular member defining first and second portions integral with the tubular member. The method includes coupling the tubular member to a flexible strand, inserting the tubular member from a first side of the soft tissue to a second side of soft tissue such that a first portion of the tubular member exits the second side of the soft tissue and a second portion of the tubular member remains inside the soft tissue, tensioning the flexible strand, deforming the first portion of the tubular member to an anchoring shape, and forming a vascularization conduit from the second portion of the tubular member.

In another aspect, the soft tissue repair method includes inserting a flaccidly deformable tubular member through a meniscus, the tubular member having first and second portions, traversing a meniscal defect with the second portion, and anchoring the tubular member to an outer surface of the meniscus with the first portion of the tubular member.

In a further aspect, the soft tissue repair method includes passing a shaft of an inserter through a longitudinal bore of a flaccidly deformable tubular member, inserting the deformable tubular member axially through soft tissue until a first portion of the tubular member is outside an outer surface of the soft tissue and a remaining portion extends axially inside the soft tissue, and deforming the first portion into an anchor on the outer surface of the soft tissue.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 2A is an environmental side view illustrating a flexible tubular member loaded on an inserter for insertion through soft tissue;

FIG. 2B is an environmental side view illustrating a flexible tubular member inserted through soft tissue such that a first portion of the tubular member is outside an outer surface of the soft tissue;

FIG. 2C is an environmental side view illustrating tensioning a flexible strand to deform the first portion of the tubular member;

FIG. 2D is an environmental side view illustrating further tensioning a flexible strand to form an anchor from the first portion of the tubular member;

FIG. 3 is a perspective view of an inserter according to the present teachings; and FIG. 4 is a perspective view of a flexible tubular member loaded on the inserter of FIG. 3.

DESCRIPTION OF VARIOUS ASPECTS

The following description is merely exemplary in nature and is in no way intended to limit the present teachings, applications, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic or other procedures.

Figure 1:
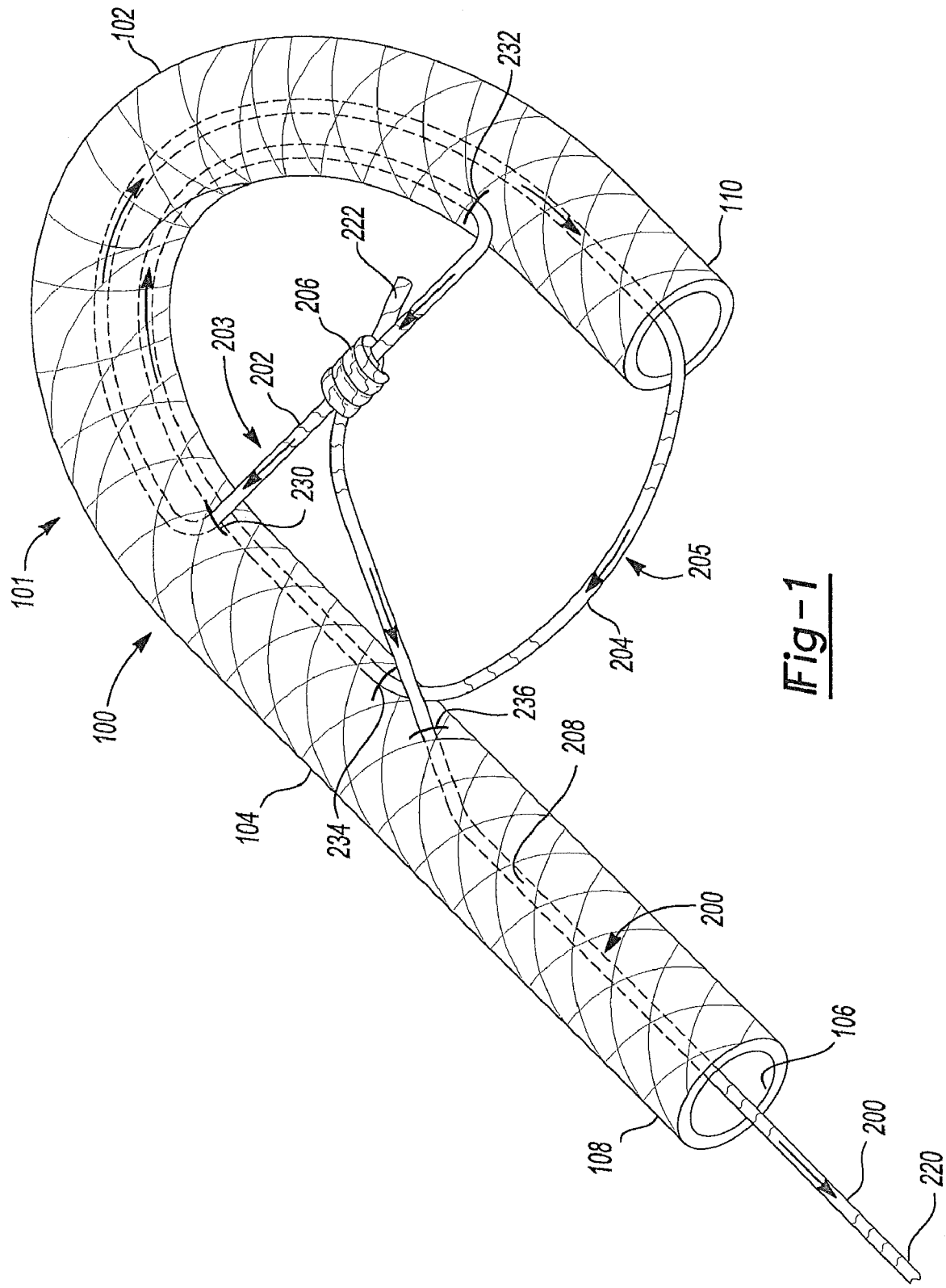
FIG. 1 is a perspective view of a flexible tubular member coupled to a flexible strand according to the present teachings, the tubular member shown with a first portion deformed.

An exemplary soft tissue repair device 101 according to the present teachings is illustrated in FIG. 1. The repair device 101 can include an elongated flexible member 100 in the form of a flaccid and deformable hollow sleeve or tubular member with a longitudinal inner bore 106 and first and second ends 108, 110. The repair device 101 can also include an elongated flexible strand 200, such as a suture, coupled to the flexible member 100. The flexible strand 200 can have first and second ends 220, 222.

The flexible member 100 can be made of resorbable or non-resorbable materials, including braided suture, woven/braided from biocompatible materials or fibers, such as, for example, polymer, polyester, polyethylene, cotton, silk, harvested vascular structures, or other natural or synthetic materials. The flexible member 100 can have any properties that allow the flexible member 100 to change shape or deform. The flexible member 100 can be, for example, compliant, flexible, foldable, squashable, squeezable, deformable, limp, flaccid, elastic, low-modulus, soft, spongy, perforated or any other flexible member which can change shape.

In some aspects, the flexible member 100 can be coated with biological or biocompatible coatings, and it can also be soaked in platelets and other biologics, which can be easily absorbed by the flexible member 100 in particular when, for example, the flexible member 100 is made from spongy, absorbent material. It should be understood by the above description that the flexible member 100 cannot pierce or otherwise penetrate tissue either with the first and second ends 108, 110 or with any portion thereof. The strand member 200 can be made of braided filaments or fibers of biocompatible material, including natural and synthetic fibers, such as cotton, silk, polymer, polyester, polyethylene, suture, and other materials.

Referring to FIGS. 3 and 4, the flexible member 100 can be loaded on the external surface of an inserter 300. The inserter 300 can include a shaft portion 302 and pointed or sharp tip 304. The inserter 300 can pass through the longitudinal inner bore 106 of the flexible member 100, as shown in FIG. 4, for guiding the flexible member 100 through soft tissue. Other inserters can also be used, such as, for example, the inserters described in the above cross-referenced and incorporated by reference patent applications, for example. The inserter 300 can include an external longitudinal guiding groove 302 for guiding a portion of the strand member 200.

The strand member 200 can be coupled to the flexible member 100 such that tensioning the strand member 200 by pulling on a free end 220 of the strand member 200 causes a first portion 102 of the flexible member to deform to a U-shape, as shown in FIG. 2C. Further tensioning of the strand member 200 causes the first portion 102 to deform to a bulkier, bunched-up, ball-like shape or anchoring shape that can serve as an anchor outside soft tissue 80, as shown in FIG. 2D and discussed below. The anchoring shape of the first portion 102 has a width W1 that is greater that the width W2 of the second portion 104 and of the opening formed in the tissue by the introduction of the flexible member 100 into the tissue 80, and prevents the first portion 102 of the flexible member 100 from re-entering the soft tissue and be pulled through the incision, thereby anchoring the flexible member 100 to the soft tissue 80. The remaining second portion 104 of the flexible member 100 can remain elongated with a substantially straight or curved or tortuous shape that forms a vascularization conduit bridging a soft tissue defect 82, and/or providing a vascularization path between vascular and avascular portions of the soft tissue 80, as discussed below.

An exemplary aspect of coupling the strand member 200 to the flexible member 100 to deform the first portion 102 is illustrated in FIG. 1, after partial tensioning. The strand member 200 can define intersecting and reducible-length loops 203, 205 passing through the inner bore 106 of the flexible member 100 and having external segments 202, 204. The first external segment 202 can extend outside the bore 106 from openings 230, 232 of the flexible member 100. The second external segment 204 can extend outside the bore 106 from an opening 234 to the opening at the second end 110 of the flexible member 100. The first end 220 of the strand member 200 can exit through the opening of the first end 106 of the flexible member 100, and the second end 222 of the strand member 200 can be coupled to the first external segment 202 with a slip knot 206. Tensioning the strand member 200 by pulling the first end 220 of the strand member 200 can reduce the length the external segments 202, 204 and associated strand loops 203, 205 allowing the first portion 102 to deform to the shape shown in FIG. 2D. A third segment 208 of the strand member 200 can extend through the inner bore 106 along the second portion 104 from an opening 236 to the opening of the first end 108 of the flexible member 100.

Figure 2E:
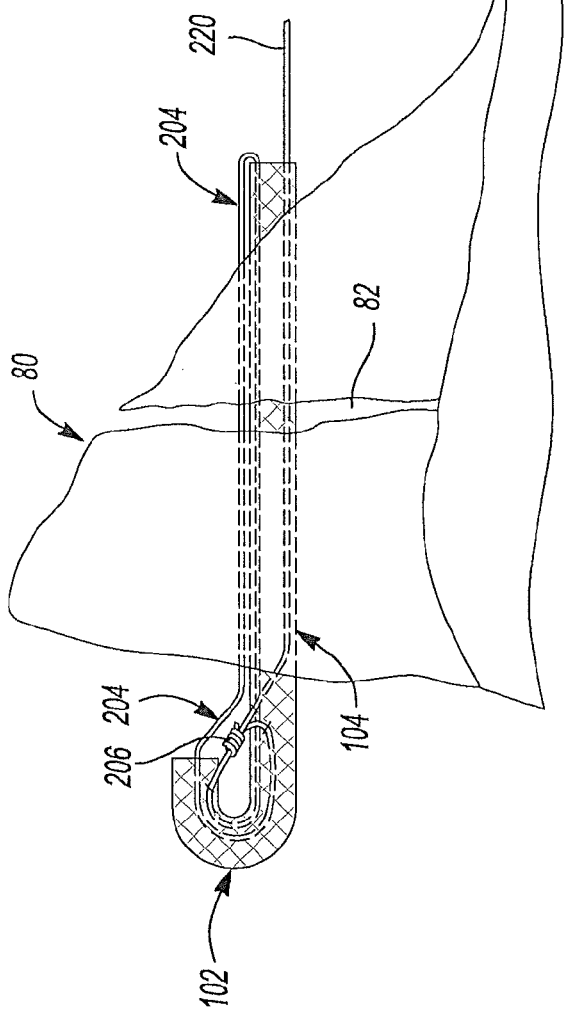
FIG. 2E is an environmental side view illustrating tensioning a flexible strand to deform the first portion of the tubular member.
Figure 2F:
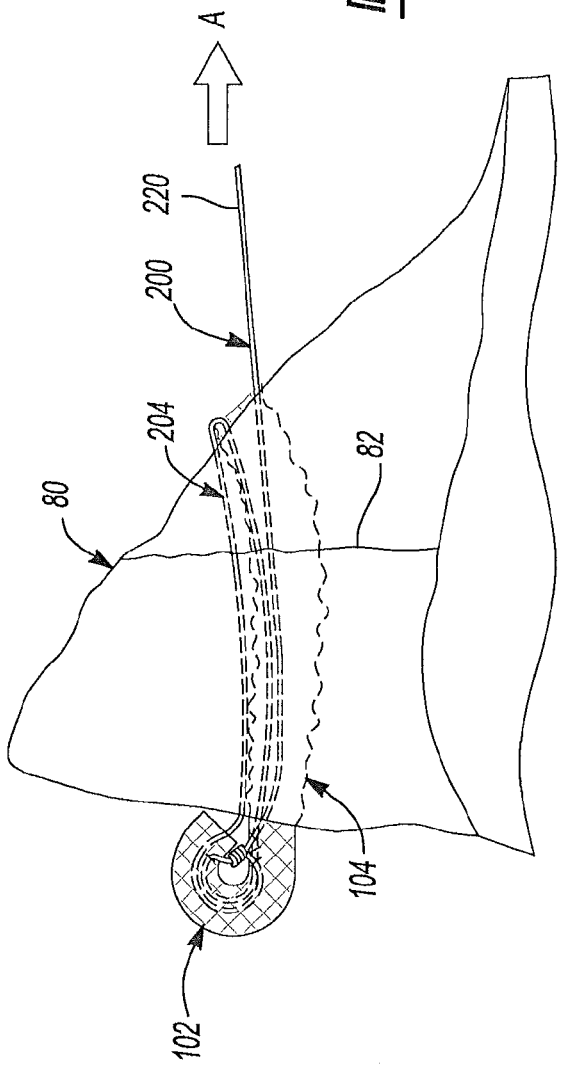
FIG. 2F is an environmental side view illustrating further tensioning of the flexible strand of FIG. 2D to form an anchor from the first portion of the tubular member.

An alternative aspect of coupling the strand member 200 to the flexible member 100 to deform the first portion 102 is illustrated in FIGS. 2E-F. In this aspect, the second external segment 204 can extend between the first and second ends 108, 110 of the flexible member 100. Tensioning the strand member 220 can cause some curving of the second portion 104, as shown in FIG. 2F.

The soft tissue repair device 101 can be used to repair a soft tissue defect 82, such as, for example, a tear, or other weakness in fibrous soft tissue 80, such as in meniscal tissue, cartilage, muscle or other fibrous tissue under the skin. In the exemplary illustration of FIGS. 2A-2D, the soft-tissue repair assembly 100 is illustrated for meniscal repair and vascularization. The second portion 104 of the flexible member can serve as a conduit between vascular and avascular regions of the meniscus on opposite sides of the defect 82 for conducting native or endogenous biological materials between first and second areas of the tissue, such as, for example, between healthy tissue and injured or torn tissue, or between areas of different vascularity, such as between red-red (vascular), red-white (semi-vascular) and white (avascular) tissue areas of a meniscus. The second portion 104 can provide a vascularity path in the soft tissue 80 for facilitating healing or repair. Additionally, biological materials in the form of platelet gels can be deposited in the flexible member 100 before implantation, as another mechanism of biological material delivery, including nutrient material delivery.

The first portion 102 of the flexible member 100 can serve as an anchor implanted on an outer surface 84 of the soft tissue 80. The implanted shape of the first portion 102 of the flexible member 102 can be of a bulkier or ball-like shape with length to width ratio close to one, as illustrated in FIG. 2D, for snugly securing the flexible member 100 on the outer surface of the soft tissue 80. The implanted shape of the first portion 102 can have bigger overall width or enclosed cross-sectional area or volume than the second portion 104 such that the first portion 102 cannot be pulled out of the same opening through which it was originally inserted. The first portion 102 can retain its bulkier shape after implantation, even after the tension on the strand portion 106 is removed.

Referring to FIGS. 2A-2D, the repair device 101 can be loaded on the inserter 300 and passed from a first surface 86 of the soft tissue 80 through the defect 82 and again through the tissue 80 until the first portion 102 of the flexible member 100 is outside a second surface 84 of the soft tissue 80 in a substantially elongated (straight or curved) configuration, as shown in FIG. 2B. Tensioning the strand member 200 by pulling in the direction of arrow A, deforms the first portion 102 into its anchor-like bulkier shape, as shown in FIGS. 2C and 2D. The second portion 104 can remain elongated (straight or curved) and form a vascularization conduit for the soft tissue 80.

It will be appreciated that multiple soft tissue repair devices 101 can be used by repeating the above procedure for repairing a soft tissue defect as described in the patent applications cross-referenced above. The present teachings provide an easy to use and effective method for repairing soft tissue with an integral device that provides anchoring and vascularization upon implantation.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings as defined in the following claims.

What is claimed is:

1. A soft tissue repair method comprising:
providing a flaccid tubular member having a longitudinal bore, and a first end portion and a second end portion,
passing a flexible strand through the tubular member, inserting the tubular member from a first side of the soft tissue to a second side of the soft tissue, such that the first end portion of the tubular member exits the second side of the soft tissue and the second end portion of the tubular member member remains inside the soft tissue;

deforming the first end and adjacent first end portion of the tubular member to a U-shaped anchor by tensioning the flexible strand; and forming a vascularization conduit from the second end and adjacent second end portion of the tubular member.

2. The method of claim 1, wherein coupling the tubular member to a flexible strand includes:

passing the flexible strand through the second end portion of the tubular member; and forming a strand loop through the first end portion of the tubular member.

3. The method of claim 1, wherein further tensioning the strand member deforms the U-shaped anchor to a ball-like shape.

4. The method of claim 1, wherein the vascularization conduit is elongated.

5. The method of claim 1, further comprising loading the tubular member on an inserter.

6. The method of claim 5, wherein loading the tubular member on an inserter includes passing the inserter through the longitudinal bore of the tubular member.

7. The method of claim 1, further comprising traversing a soft tissue defect with the vascularization conduit.

8. The method of claim 1, further comprising bridging vascular and avascular portions of the soft tissue with the vascularization conduit.

9. The method of claim 1, wherein tensioning the flexible strand includes reducing a length of a loop formed by the flexible strand through the first end portion of the tubular member.

10. A soft tissue repair method comprising:

inserting a flaccidly deformable tubular member through a meniscus, the tubular member having a first end portion and a second end portion;

traversing a meniscal defect with the second end portion such that the first end portion exits the meniscal defect;

deforming the first end portion to a U-shaped anchor by tensioning a flexible strand; and anchoring the tubular member to an outer surface of the meniscus with the U shaped anchor of the tubular member.

11. The method of claim 10 further comprising the flexible strand forming a loop of reducible length through the first end portion.

12. The method of claim 10, wherein traversing the meniscal defect with the second end portion includes forming a vascularization conduit between opposing sides of the meniscal defect.

13. The method of claim 10, wherein traversing the meniscal defect with the second end portion includes creating a vascularization path between vascular and avascular portions of the meniscus.

14. A soft tissue repair method comprising:

passing a shaft of an inserter through a longitudinal bore of a flaccidly deformable tubular member;

inserting the deformable tubular member axially through soft tissue until a first end portion of the tubular member is outside an outer surface of the soft tissue and a remaining second end portion of the tubular member extends axially inside the soft tissue; and deforming the first end portion into a U-shaped anchor on the outer surface of the soft tissue by reducing a length of flexible strand looped around the first end portion.

15. The method of claim 14, wherein reducing the length of flexible strand looped around the first end portion includes tensioning the flexible strand.

16. The method of claim 14, further comprising forming a vascularization path through the soft tissue with the remaining second end portion.

17. The method of claim 14, wherein forming the vascularization path includes bridging vascular and avascular regions of the soft tissue with the remaining second end portion.

18. The method of claim 14, wherein forming the vascularization path includes traversing a soft tissue defect with the remaining second end portion.

* * * * *

UNITED STATES PATENT AND TRADEMARK OFFICE
CERTIFICATE OF CORRECTION

| | | |
|---|---|---|
| PATENT NO. | : 7,857,830 B2 | Page 1 of 1 |
| APPLICATION NO. | : 11/869440 | |
| DATED | : December 28, 2010 | |
| INVENTOR(S) | : Kevin T. Stone et al. | |

It is certified that error appears in the above-identified patent and that said Letters Patent is hereby corrected as shown below:

Column 5
Line 5, delete second occurrence of "member".

Signed and Sealed this
Nineteenth Day of July, 2011

David J. Kappos
*Director of the United States Patent and Trademark Office*